US009510572B2

(12) United States Patent
Aldana et al.

(10) Patent No.: US 9,510,572 B2
(45) Date of Patent: Dec. 6, 2016

(54) **CONTAINED SYSTEMS TO PROVIDE REPRODUCTIVE HABITAT FOR *HERMETIA ILLUCENS***

(71) Applicant: ENTERRA FEED CORPORATION, Vancouver (CA)

(72) Inventors: Juan Aldana, Victoria (CA); Edna Quan, Vancouver (CA); Andrew Vickerson, Vancouver (CA); Brad Marchant, Vancouver (CA); Oliver Kaulfuss, New Westminster (CA); Reed Radley, Vancouver (CA)

(73) Assignee: ENTERRA FEED CORPORATION, Vancouver (CA)

( * ) Notice: Subject to any disclaimer, the term of this patent is extended or adjusted under 35 U.S.C. 154(b) by 60 days.

(21) Appl. No.: 14/397,679

(22) PCT Filed: May 7, 2013

(86) PCT No.: PCT/CA2013/000457
§ 371 (c)(1),
(2) Date: Oct. 29, 2014

(87) PCT Pub. No.: WO2013/166590
PCT Pub. Date: Nov. 14, 2013

(65) Prior Publication Data
US 2015/0122182 A1    May 7, 2015

Related U.S. Application Data

(60) Provisional application No. 61/643,728, filed on May 7, 2012.

(51) Int. Cl.
*A01K 67/00* (2006.01)
*A01K 67/033* (2006.01)

(52) U.S. Cl.
CPC .................. *A01K 67/033* (2013.01)

(58) Field of Classification Search
CPC ..................................... A01K 67/033
(Continued)

(56) References Cited

U.S. PATENT DOCUMENTS 3,939,883 A    2/1976   Harrell
4,850,305 A *  7/1989   Georgi ................ A01K 67/033
                                                119/303

(Continued)

FOREIGN PATENT DOCUMENTS

CA      2834412       11/2012
CN    201185612 Y     1/2009
(Continued)

OTHER PUBLICATIONS

Zhang, J., et al., "An artificial light source influences mating and oviposition of black soldier flies," *Hernetia illucens*, Journal of Insect Science, 2010, vol. 10, Article 202, 1-7 (the entire article).

(Continued)

*Primary Examiner* — Joshua Rodden
(74) *Attorney, Agent, or Firm* — Casimir Jones S.C.

(57) ABSTRACT

An apparatus and method of inducing black soldier flies to emerge, mate and lay eggs is provided. The method involves exposing at least one male black soldier fly and at least one female black soldier fly to artificial light in an enclosed space The artificial light includes at least one wavelength in a visible spectrum and at least one wavelength in an ultraviolet spectrum.

17 Claims, 9 Drawing Sheets

(58) Field of Classification Search
USPC .......................................................... 119/6.6
See application file for complete search history.

(56) References Cited

U.S. PATENT DOCUMENTS

| | | | |
|---|---|---|---|
| 5,158,497 A * | 10/1992 | Rossignol | A01K 49/00 119/6.5 |
| 5,759,224 A | 6/1998 | Olivier | |
| 6,244,213 B1 * | 6/2001 | Tedders | A01K 67/033 119/6.6 |
| 6,391,620 B1 | 5/2002 | Olivier | |
| 6,397,782 B1 * | 6/2002 | Cope | A01K 67/033 119/416 |
| 6,557,487 B1 | 5/2003 | Fleischmann | |
| 6,780,637 B2 | 8/2004 | Olivier | |
| 6,786,001 B1 | 9/2004 | Piper | |
| 6,938,574 B2 | 9/2005 | Zhang | |
| 8,322,305 B2 | 12/2012 | Chang | |
| 2002/0177219 A1 | 11/2002 | Olivier | |
| 2003/0143728 A1 | 7/2003 | Olivier | |
| 2003/0233982 A1 | 12/2003 | Zhang | |
| 2008/0163541 A1 | 7/2008 | Harris | |
| 2011/0081452 A1 | 4/2011 | Hem et al. | |
| 2011/0174222 A1 | 7/2011 | Lee | |
| 2011/0296756 A1 | 12/2011 | Zhang | |
| 2012/0187041 A1 | 7/2012 | Popa | |
| 2014/0020630 A1 * | 1/2014 | Courtright | A01K 29/00 119/6.6 |

FOREIGN PATENT DOCUMENTS

| | | |
|---|---|---|
| CN | 102329155 A | 1/2012 |
| CN | 101889629 B | 9/2012 |
| WO | 2010/002188 | 1/2010 |
| WO | 2012/100077 | 7/2012 |
| WO | 2013/166590 | 11/2013 |

OTHER PUBLICATIONS

Biopod: the future of food waste diversion and recycle. Black Soldier Fly Forum: Breeding BSF in captivity. Reply #22 "Re: not easy" by earthtiger, Nov. 26, 2011, retrieved from the Internet: URL: http://thebiopod.com/forum/index.php?topic=175.15 "retrieved on Jun. 20, 2013" (reply and photographs).

Tomberlin, J.K., et al., "Factors influencing mating and oviposition of black soldier flies (*Diptera stratiomyidae*) in a colony." Journal of Entomological Science. 2002. vol. 37, No. 4, pp. 345-352.

Sheppard, D. Craig, et al., Rearing Methods for the Black Soldier Fly (*Diptera strationmyidae*), J. Med. Entonnol., 39(4): 695-698 (2002).

ISR & Written Opinion from PCT/CA2013/000457 dated Aug. 2, 2013, 10 pages.

Bradley, S. W. and Sheppard, D. C. 1984. House Fly Oviposition Inhibition by Larvae of *Hermetia illucens*, the Black Soldier Fly. Journal of Chemical Ecology, 19, 853.

Erickson, M. C., M. Islam, C. Sheppard, J. Liao, and M. P. Doyle. 2004. Reduction of *Eschericia coli* 0157:H7 and *Salmonella enterica* serovar Enteritidis in chicken manure by larvae of the black soldier fly. J. Food Protection. 67: 685-690.

Furman, D. P., R. D. Young, and E. P. Catts. 1959. *Hermetia illucens* (Linnaeus) as a factor in the natural control of *Musca domestica* Linnaeus. J. Econ. Entomol. 52: 917-921. (Abstract Only).

Hogsette, J. A. 1985. New diets for production of house flies and stable flies (*Diptera muscidae*) in the laboratory. J. Econ. Entomol. 85: 2291-2294.

Liu, Q., Tomerblin, J. K., Brady, J. A., Sanford, M. R., and Yu, Z. 2008. Black Soldier Fly (*Diptera stratiomyidae*) Larvae Reduce *Escherichia coli* in Dairy Manure. Environ. Entomol. 37(6): 1525-1530.

Tomberlin, J. K., Alder, P. H., and Myers H. M. 2009. Development of the Black Soldier Fly (*Diptera stratiomyidae*) in Relation to Temperature. Environ. Entomol.38: 930-934.

Tomberlin, J.K., D. C. Sheppard & J.A. Joyce. 2002. Selected Life-History Traits of Black Soldier Flies (*Diptera stratiomyidae*) Reared on Three Artificial Diets. Ann. Entomol. Soc. Am. 95(3): 379-386.

ISR & Written Opinion from PCT/CA2014/050727 dated Oct. 22, 2014.

ISR & Written Opinion from PCT/CA2015/050653 dated Sep. 29, 2015.

EESR from European Patent Application No. 13787121.6 dated Oct. 30, 2015.

Enterra Feed Corporation. CTVNews—"Bugs Life"—Enterra Feed Corporation. Nov. 4, 2013 [online video, retrieved on Oct. 2, 2014]. Retrieved from the internet: <URL: http://www.enterrafeed.comlctv-news-bugs-lifevideo/> or from: <URL: http://www.youtube.comlwatch?v=VBHVg_tdTLM>.

Enterra Feed Corporation. Enterra Natural Fertilizer™ Product Specifications. Jul. 2014 and Jun. 2013 [online PDF document, retrieved on Oct. 2, 2014]. Retrieved from the internet: <URL: http://enterrafeed.coml wp-contentiuploadsIN atural-Fertilizer.pdf>.

Foster, S.P. et al. Behavioral manipulation methods for insect pest-management. Annual Review a/Entomology, 1997, vol. 42, pp. 123-146, ISSN: 0066-4170 (Print).

Green, T.R. et al. Applied Biochemistry and Biotechnology, online Jan. 12, 2012, Mar. 2012, vol. 166, No. 6, pp. 1381-1387.

Larde, "Investigation on Some Factors Affecting Larval Growth in a Coffee-Pulp Bed" Biological Wastes 30 (1989) 11-19.

Larde, "Recycling of Coffee Pulp by *Hermetia illucens* (*Diptera stratiomyidae*) Larvae" Biological Wastes 33 (1990) 307-310.

Myers et al. "Development of Black Soldier Fly (*Diptera stratiomyidae*) Larvae Fed Dairy Manure" Environ. Entomol. 37(1): 11-15(2008).

Newton, et al. "Using the Black Soldier Fly, *Hermetia illucens*, As a Value-Added Tool for the Management of Swine Manure" Jun. 6, 2005, https://www.cals.ncsu.edu/waste_mgt/smithfield_projects/phase2report05/cd,web%20files/A2.pdf.

Olivier, P. A. (2009) "Utilizing lower life forms for the bioconversion of putrescent waste." Black Soldier Fly Blog—Official Website.

Sheppard et al, "A value added manure management system using the black soldier fly" Bioresource Technology 50 (1994) 275-279.

Sheppard et al, "Black Soldier Fly Prepupae A Compelling Alternative to Fish Meal and Fish Oil", A Public Comment Prepared in Response to a Request by the National Marine isheries Service Nov. 15, 2007, http://www.aquacircle.org/images/pdfdokumenter/udvikling/andre/amerika/Soldier_fly_compelling_alternative_NOAA-USDA.pdf.

St. Hilaire et al, "Fish Offal Recycling by the Black Soldier Fly Produces a Foodstuff High in Omega-3 Fatty Acids", Journal of the World Aquaculture Society, vol. 38, No. 1, Mar. 2007.

St. Hilaire et al, "Fly Prepupae as a Feedstuff for Rainbow Trout, *Oncorhynchus mykiss*" Journal of the World Aquaculture Society, vol. 38, No. 2, Jun. 2007.

Temple, W.D. et al. "Use of Enterra Natural Fertilizer (Black Soldier Fly Larvae 1-20 Digestate) As a Soil Amendment." Enterra Feed Corporation, Nov. 2013 [online PDF document, retrieved on Oct. 2, 2014]. Retrieved from the internet: <URL: http://www.certifiedorgank.bc.ca/programs/osdpll-172] rass_Research_Final %20 Report.pdf>.

Tomberlin and Sheppard Lekking Behavior of the Black Soldier Fly (*Diptera stratiomyidae*), Florida Entomologist, 84(4) Dec. 2001, 729-730.

Tossell, I. "Conversation with David Suzuki leads to maggot-based animal feed." The Globe and Mail, Oct. 28, 2013 [online newspaper article, retrieved on Oct. 2, 2014]. Retrieved from the internet: <URL: http://www.theglobeandmail.comlreport-on-business/small-business/starting-outl conversation-with-david-suzuki-leads-to-maggot-based-animal-feedlarticlel5114182/>.

* cited by examiner

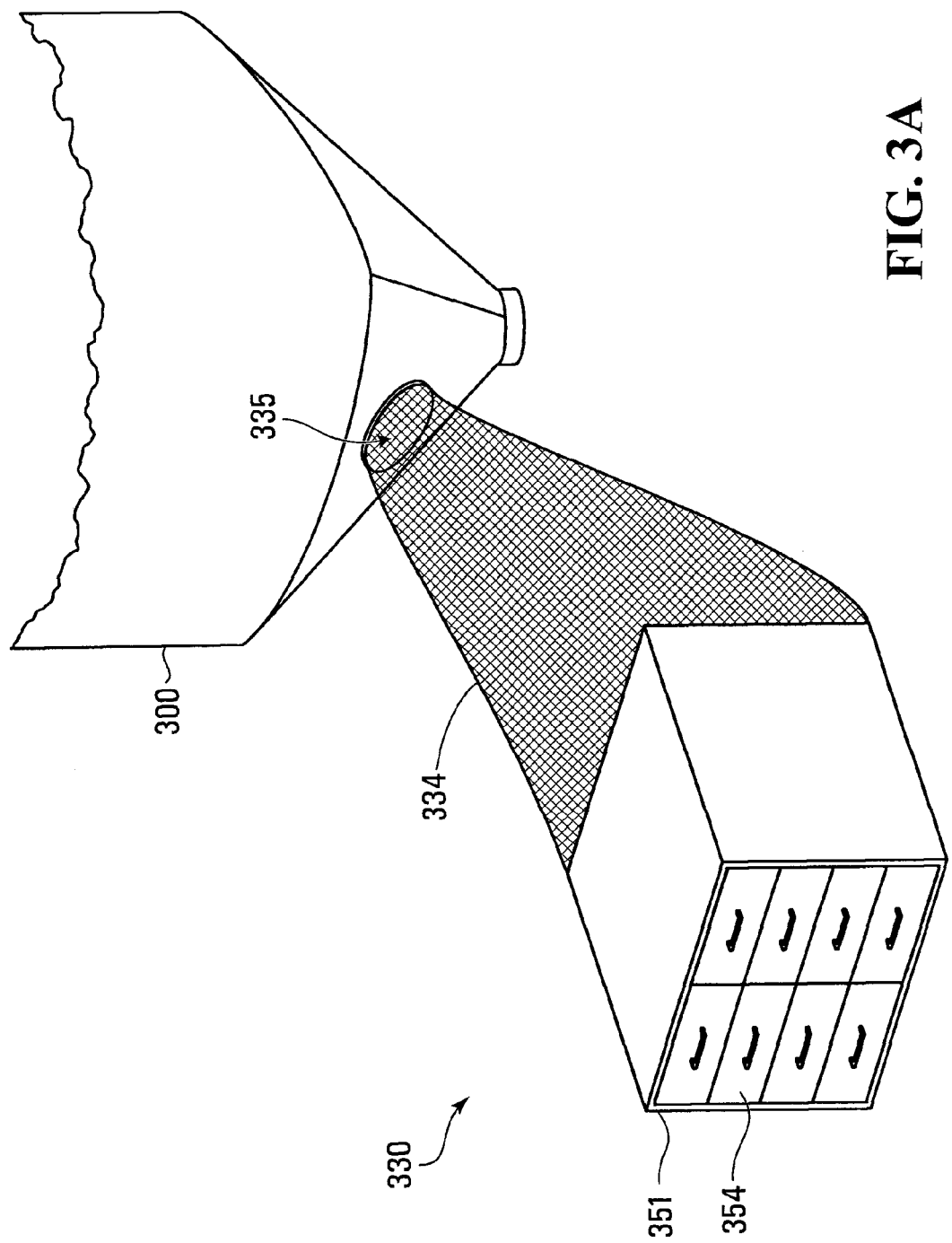

CONTAINED SYSTEMS TO PROVIDE REPRODUCTIVE HABITAT FOR *HERMETIA ILLUCENS*

CROSS REFERENCE TO RELATED APPLICATIONS

The present application is a Section 371 U.S. national stage entry of pending International Patent Application No. PCT/CA2013/000457, International Filing Date May 7, 2013, which published on Nov. 14, 2013 as Publication No. WO 2013/166590 A1, which claims the benefit of U.S. Provisional Patent Application No. 61/643,728, filed May 7, 2012, the contents of which are incorporated by reference in their entireties.

CORRESPONDING APPLICATIONS

This application claims the priority benefit of U.S. patent application No. 61/643,728 filed on May 7, 2012, the contents of which are incorporated herein by reference in their entirety.

FIELD OF THE INVENTION

The invention relates to apparatus and methods for culturing Dipteran insects, particularly *Hermetia illucens* (commonly referred to as the black soldier fly). In particular, the invention includes apparatus and methods for producing black soldier fly eggs.

BACKGROUND OF THE INVENTION

Larvae of the black soldier fly (BSF; *Hermetia illucens*; as utilized herein, BSFs means black soldier flies) are well suited to converting organic waste products, such as fruit and vegetable matter (including coffee pulp), meat and fish, bread and grains, and manures, into market-valuable products, such as livestock (terrestrial or aquatic) feed or feed ingredients, pet food, food stuffs for human consumption, and plant growth supplements. Advantages of BSFs include the following: (i) BSFs are indigenous to the Americas and are now found in many parts of the world; (ii) BSF larvae grow on a wide variety of organic waste products; (iii) BSF larvae and prepupae are high in protein and fatty acid content and self-harvesting; (iv) BSF adults do not need food and are therefore are not known as a disease vector; (v) BSF larvae demonstrate anti-pathogenic qualities (Erickson, et al. 2004; Liu, et al. 2008); and (vi) BSF larvae produce stable colonies because they deter colonization from other insect species (Bradley and Sheppard, 1984) and can survive in a variety of environmental conditions.

As a member of the Family Stratiomyidae, the BSF goes through full metamorphosis during its lifespan. This includes the egg, larval, pupae and adult life cycle stages. Larvae will hatch from the egg stage after 48-72 hours and go through five instars (larval stages) before reaching the pupae stage. The first instar (L1) will molt into the second instar (L2) within 4-5 days and generally reach the pupae stage within a further 12-30 days, and for example, within 12-18 days, depending on temperature, humidity, type of feed, quantity of feed, frequency of feeding, mixture of feed ingredients, moisture of feed, starter diet, finishing diet and consistency of feed. Between the fifth instar (L5) and the pupae stage is the prepupae stage, where BSF larvae seek a drier environment, for example an environment that is less saturated or less than 100% moisture, to complete the metamorphosis stage of its life cycle. Accordingly, prepupae will crawl away from their "juvenile" feeding grounds, i.e., the organic wastes. This dispersal behavior translates into a "self-harvesting" mechanism which allows for a convenient collection of prepupae. Self-harvesting is further facilitated by the fact that BSF larvae are negatively phototactic and thus light can be used to encourage migration in desired directions upon user demand. The pupae stage generally lasts 9-20 days, and for example, 7-10 days depending on factors such as, for example, movement, proximity to other moving pupae, level of light, temperature and humidity, following which the adult fly will emerge. Adult BSFs mate and gravid female BSFs will lay eggs (i.e., "oviposit") for the next generation. The life span of an adult BSF is generally 6-15 days, and, for example, 7-10 days, depending on humidity (e.g., 50-90%) and/or temperature (e.g., 22-35° C.) and stored energy, such as quantities and profiles of protein and fat. The timeline for the aforementioned life cycle is approximate and depends on environmental conditions and food supply. For example, it has been reported that limited food supply can extend the larval period to 4 months (Furman et al., 1959).

Under appropriate conditions, gravid female BSF adults will oviposit eggs approximately 24-72 hours after mating. Eggs are generally oviposited in tight, narrow spaces, such as blocks of cardboard with flutes oriented in any direction. Females are typically attracted to oviposition sites with pungent odours, as this usually indicates a potential food source for BSF offspring. BSF adults require specific environmental conditions to induce mating behaviors, including specific ranges of light, space, temperature and humidity. BSF will survive and mate at temperatures between 22° C. and 35° C. and humidity levels between 30% and 90%, and for example, BSF will survive and mate at an ambient air temperature of approximately 25° C.-30° C. with a relative humidity of approximately 60-80%. It has been reported that a BSF colony can be maintained at 22° C. (Tomberlin and Sheppard, 2002) and that the upper limit for optimal development of the BSF is between 30-36° C. (Tomberlin et al., 2009). A study measuring BSF mating and oviposition reported that 80% percent of egg clutches were deposited when humidity exceeded 60% (Tomberlin and Sheppard, 2002).

Direct sunlight has been reported to encourage mating (but not ovipositing) in BSF (Tomberlin and Sheppard, 2002). Accordingly, BSF mating is limited by weather conditions and time of year for non-tropical regions. Several artificial lights have been tested in lieu of sunlight. A 40 W Sylvania Gro Lux® (Orson Sylvania Inc., Danvers, Mass.) and a 430 W Pro Ultralight Light System® (Hydrofarm Inc. Petaluma, Calif.) were each reported to be unsuccessful in eliciting mating behavior (Tomberlin and Sheppard, 2002). Similarly, a 450 W (measured light intensity of 160 $\mu mol \cdot m^{-2} \cdot s^{-1}$, 50 cm below the bulb) rare earth light (Engineering University Infrared Technology Research Institute, Harbin, Heilung-Kiang China) reportedly failed to stimulate mating (Zhang et al., 2010). To date, the only artificial light source that has been reported to stimulate mating in BSF is a 500 W (measured light intensity of 160 $\mu mol \cdot m^{-2} \cdot s^{-1}$, 50 cm below the bulb) quartz-iodine lamp, which yielded 61.9% mating success compared to natural sunlight (Zhang et al., 2010).

Additionally, traditional BSF rearing systems consist of cages or greenhouses that require workers to enter or reach inside the cage with adults to add new prepupae to a pupation chamber, to collect eggs deposited on cardboard blocks, and to collect mortalities by sweeping or vacuuming.

Requiring human workers to enter and exit the cage is disruptive because it allows flies to escape, disrupts mating behavior, potentially stresses flies by stimulating flight reactions and inadvertently leads to collecting live flies mortalities.

SUMMARY

Various embodiments of the invention provide a method of inducing black soldier flies (BSFs) to mate is provided. The method involves exposing at least one male BSF and at least one female BSF to artificial light. The artificial light includes at least one wavelength in a visible spectrum and at least one wavelength in an ultraviolet spectrum. The method detailed herein may include an artificial light that has a visible and UV light intensity that is less than 400 $\mu mol \cdot m^{-2} \cdot s^{-1}$ and less than 100 $\mu W \cdot cm^{-2} \cdot s^{-1}$, respectively. Optionally, the at least one wavelength in the visible spectrum may be produced using a 300 to 500 W quartz-iodine lamp and the at least one wavelength in the ultraviolet spectrum may be produced using a 50 W halogen lamp.

Various embodiments of the invention provide an apparatus for inducing BSFs to mate. The apparatus includes a mating chamber for receiving at least one male BSF and at least one female BSF. The apparatus further includes at least one artificial light source, wherein the at least one artificial light source is configured to illuminate the chamber with at least one wavelength in the visible spectrum and at least one wavelength in the ultraviolet spectrum. The artificial light source may be configured to emit light with a visible light intensity that is less than 400 $\mu mol \cdot m^{-2} \cdot s^{-1}$. The at least one wavelength in the visible spectrum may be produced using a 300 to 500 W quartz-iodine lamp. The at least one wavelength in the ultraviolet spectrum may be produced using a 50 W halogen lamp.

Various embodiment of the invention provide an apparatus for collecting black soldier fly eggs. The apparatus includes a mating chamber defined by at least one mating chamber wall, wherein the at least one mating chamber wall further defines a mating chamber opening for admitting BSFs into the mating chamber. The apparatus further includes at least one artificial light source configured to illuminate the mating chamber with at least one wavelength in the visible spectrum and at least one wavelength in the ultraviolet spectrum. The apparatus may further include an oviposition chamber in communication with the mating chamber. The oviposition chamber may be positioned within the mating chamber. The oviposition chamber may be defined by at least one oviposition chamber wall, wherein the at least one oviposition chamber wall further defines an oviposition chamber opening for receiving gravid BSFs into the oviposition chamber. The oviposition chamber may include an oviposition shade for shading gravid BSFs from the at least one artificial light source, and a collector for collecting BSF eggs oviposited by gravid BSFs. The artificial light source may be configured to provide visible light with a visible light intensity that is less than about 400 $\mu mol \cdot m-2 \cdot s-1$ and ultraviolet light with an ultraviolet light intensity that is less than about 100 $\mu W \cdot cm \cdot -2 \cdot s-1$. The artificial light source may include a 300 to 500 W quartz-iodine lamp for generating the at least one wavelength in the visible spectrum and a 50 W halogen lamp for producing the at least one wavelength in the ultraviolet spectrum. The collector may include a plurality of substantially vertical flutes or tubes. The oviposition chamber may further include an attractant for attracting gravid BSFs. The oviposition may further include an upper drawer and a lower drawer, wherein each of the upper drawer and the lower drawer is configured to open to the exterior of the mating chamber, and wherein the collector is situated on the upper drawer and the attractant is situated on the lower drawer.

The apparatuses described above may further include a pupation chamber in communication with the mating chamber via the mating chamber opening. The pupation chamber may include a pupation chamber shade for shading pupae from the artificial light source. The pupation chamber may be positioned within the mating chamber and include an opening for permitting emergent BSFs to exit the pupation chamber into the mating chamber. Alternatively, communication between the pupation chamber and the mating chamber may be provided by a conduit. The apparatuses may further include a blower in communication with the conduit for blowing BSFs in the conduit toward the mating chamber. The conduit may include a check valve through which BSFs must pass in order to access the mating chamber. The check valve may open in response to pressure, or a force, generated by the blower. The apparatuses may further include a conduit light source configured to illuminate a portion of the conduit to attract migration of BSFs from the pupation chamber to the conduit. The conduit may include a one-way passage or duct, e.g. a funnel, through which BSFs must pass in order to access the mating chamber, wherein the funnel tapers toward the mating chamber.

Various embodiments of the invention provide kits for constructing the apparatuses described above.

Various embodiments of the invention provide a method for converting organic waste material. The method includes isolating BSF eggs using the apparatus described above, distributing the BSF eggs in an environment containing organic waste material, and maintaining the BSF eggs in the environment until the BSF eggs hatch to become BSF larvae capable of converting organic waste material. The BSF eggs may be maintained in a digester containing organic waste material.

Various embodiments of the invention provide a method of isolating BSF eggs. The method includes the following steps: a) providing at least one male BSF and at least one female BSF to a mating chamber; b) illuminating the mating chamber with artificial light comprising at least one wavelength in a visible spectrum and at least one wavelength in an ultraviolet spectrum to induce the at least one male BSF and the at least one female BSF to mate; c) attracting gravid BSFs to an oviposition chamber in communication with the mating chamber, wherein the oviposition chamber is configured to receive eggs from the gravid BSFs; d) shading gravid BSFs in the oviposition chamber to induce the gravid BSFs to oviposit eggs; and e) collecting eggs oviposited by the gravid BSFs. The at least one artificial light may include visible light having a visible light intensity that is less than 400 $\mu mol \cdot m-2 \cdot s-1$ and ultraviolet light having an ultraviolet light intensity that is less than 100 $\mu W \cdot cm \cdot -2 \cdot s-1$. The at least one artificial light source may include a 300 to 500 W quartz-iodine lamp for generating the at least one wavelength in the visible spectrum and a 50 W halogen lamp for producing the at least one wavelength in the ultraviolet spectrum. Step a) may further include providing at least one male BSF pupa and at least one female BSF pupa into a pupation chamber in communication with the mating chamber and shading the at least one male BSF pupa and the at least one female BSF pupa from the artificial light source. The method may further include removing the at least one male BSF and the at least one female BSF from the mating chamber once the at least one male BSF and the at least one female BSF are deceased, wherein living BSFs are not removed from the mating chamber, which may include opening a sealable aperture on the mating chamber. Collecting eggs oviposited by the gravid BSFs may include collecting eggs in a plurality of substantially vertical flutes or tubes positioned in the oviposition chamber. Attracting gravid BSFs to the oviposition chamber may include supplying an attractant for attracting the gravid female BSFs. The attractant may be an approximately saturated 1:1 mixture of Gainesville diet and BSF castings.

Various embodiments of the inventions provide a method for converting organic waste material. The method includes isolating BSF eggs according to the method described above, distributing the isolated BSF eggs in an environment containing organic waste material, and maintaining the BSF eggs in the environment until the BSF eggs hatch to become BSF larvae capable of converting organic waste material. The BSF eggs may be maintained in a digester containing organic waste material.

Various embodiment of the invention provide a method of isolating BSF eggs. The method involves inputting at least one male BSF and at least one female BSF into a mating chamber. The method further involves inducing the at least one male BSF and the at least one female BSF to mate by illuminating the interior of the mating chamber with artificial light having at least one wavelength in a visible spectrum and at least one wavelength in an ultraviolet spectrum. The method further involves providing an oviposition chamber that is connected to the mating chamber. The oviposition chamber is adapted for BSF eggs to be oviposited by at least one gravid female BSF. The oviposition chamber includes a passage for the at least one gravid female BSF to travel from the interior of the mating chamber to the oviposition chamber. The oviposition chamber further includes a shade positioned to shade ovipositing female BSFs from the artificial light. The oviposition chamber further includes a collector for receiving the BSF eggs from the gravid female BSF. The method detailed herein further involves collecting the BSF eggs.

The method may include an artificial light that has a visible and UV light intensity that is less than 400 $\mu mol \cdot m^{-2} \cdot s^{-1}$ and less than 100 $\mu W \cdot cm^{-2} \cdot s^{-1}$, respectively. Optionally, the at least one wavelength in the visible spectrum may be produced using a 300 to 500 W quartz-iodine lamp and the at least one wavelength in the ultraviolet spectrum may be produced using a 50 W halogen lamp.

The method may involve inputting at least one male BSF pupa and at least one female BSF pupa into a pupation chamber. The pupation chamber may include a second passage connecting the pupation chamber to the interior of the mating chamber. The pupation chamber may include an opening for inputting the at least one male BSF pupa and the at least one female BSF pupa into the pupation chamber. The pupation chamber may include a second shade for shading the at least one male BSF pupa and the at least one female BSF pupa from the artificial light source. Further, the method may involve removing the at least one male BSF and the at least one female BSF from the mating chamber once the at least one male BSF and the at least one female BSF are deceased, wherein living BSFs are not removed from the mating chamber. Further, the method may involve collecting the BSF eggs by using a sealable aperture on the mating chamber. Optionally, the collector includes a plurality of substantially vertical flutes or tubes. Further, and optionally, the oviposition chamber includes an attractant for attracting gravid female BSFs.

The method may further include a collector that is situated on an upper drawer that provides outside access to the interior of the mating chamber. Optionally, the attractant is situated on a lower drawer that provides outside access to the interior of the mating chamber. Further, the method may involve opening the upper drawer and removing the collector. Optionally, the attractant is approximately a saturated 1:1 mixture of Gainesville diet and BSF castings.

Various embodiments of the invention provide an apparatus for isolating BSF eggs is provided. The apparatus includes a mating chamber having an opening for inputting at least one BSF and at least one female BSF into the mating chamber. The apparatus further includes at least one artificial light source configured to illuminate the inside of the mating chamber with at least one wavelength in a visible spectrum and at least one wavelength in an ultraviolet spectrum. The apparatus further includes an oviposition chamber having access to the interior of the mating chamber. The apparatus further includes a shade for shading ovipositing BSFs from the at least one artificial light source. Further, the apparatus includes a collector for receiving the BSF eggs from the gravid female BSFs. The apparatus detailed herein may include an artificial light source that provides a visible and UV light intensity that is less than 400 $\mu mol \cdot m^{-2} \cdot s^{-1}$ and less than 100 $\mu W \cdot cm^{-2} \cdot s^{-1}$, respectively. Optionally, the at least one wavelength in the visible spectrum may be produced using a 300 to 500 W quartz-iodine lamp and the at least one wavelength in the ultraviolet spectrum may be produced using a 50 W halogen lamp. The apparatus detailed herein may include a pupation chamber having an interior that is connected to the opening and a second shade for shading the BSF pupae in the pupation chamber from the at least one artificial light source. Further, the apparatus may include means for removing dead BSFs from the mating chamber. The means for removing dead BSFs from the mating chamber may include an interior surface of the mating chamber that tapers to a sealable opening on an underside of the mating chamber. Further, the collector may include a plurality of substantially vertical flutes or tubes. Further, the oviposition chamber may include an attractant for attracting gravid female BSFs. Further, the apparatus may include an upper drawer and a lower drawer, each providing outside access to the interior of the mating chamber, wherein the collector is situated on the upper drawer and the attractant is situated on the lower drawer.

Various embodiments of the invention provide a method for converting organic waste material. The method involves isolating BSF eggs according to the methods detailed herein. The method further involves distributing the BSF eggs in an environment containing organic waste material. The method further involves maintaining the BSF eggs in the environment until the BSF eggs hatch to become BSF larvae capable of converting organic waste material.

Various embodiments of the invention provide a method for converting organic waste material. The method involves isolating BSF eggs using the apparatus detailed herein; distributing the BSF eggs in an environment containing organic waste material; and maintaining the BSF eggs in the environment until the BSF eggs hatch to become BSF larvae capable of converting organic waste material. The methods detailed herein may involve maintaining the BSF eggs in a digester that contains organic waste material.

BRIEF DESCRIPTION OF THE DRAWINGS

FIG. 3A is a perspective view of a pupation chamber utilizing a drawer system for use with various embodiments of the invention.

DETAILED DESCRIPTION

Various embodiments of the invention provide an apparatus and methods for producing and isolating BSF eggs in a self-contained environment, including the inducement of mating and the convenient isolation and collection of eggs with minimal disruption of fly behaviors. The following exemplary embodiments are provided for illustrative purposes, and are not intended to be limiting.

Figure 1:
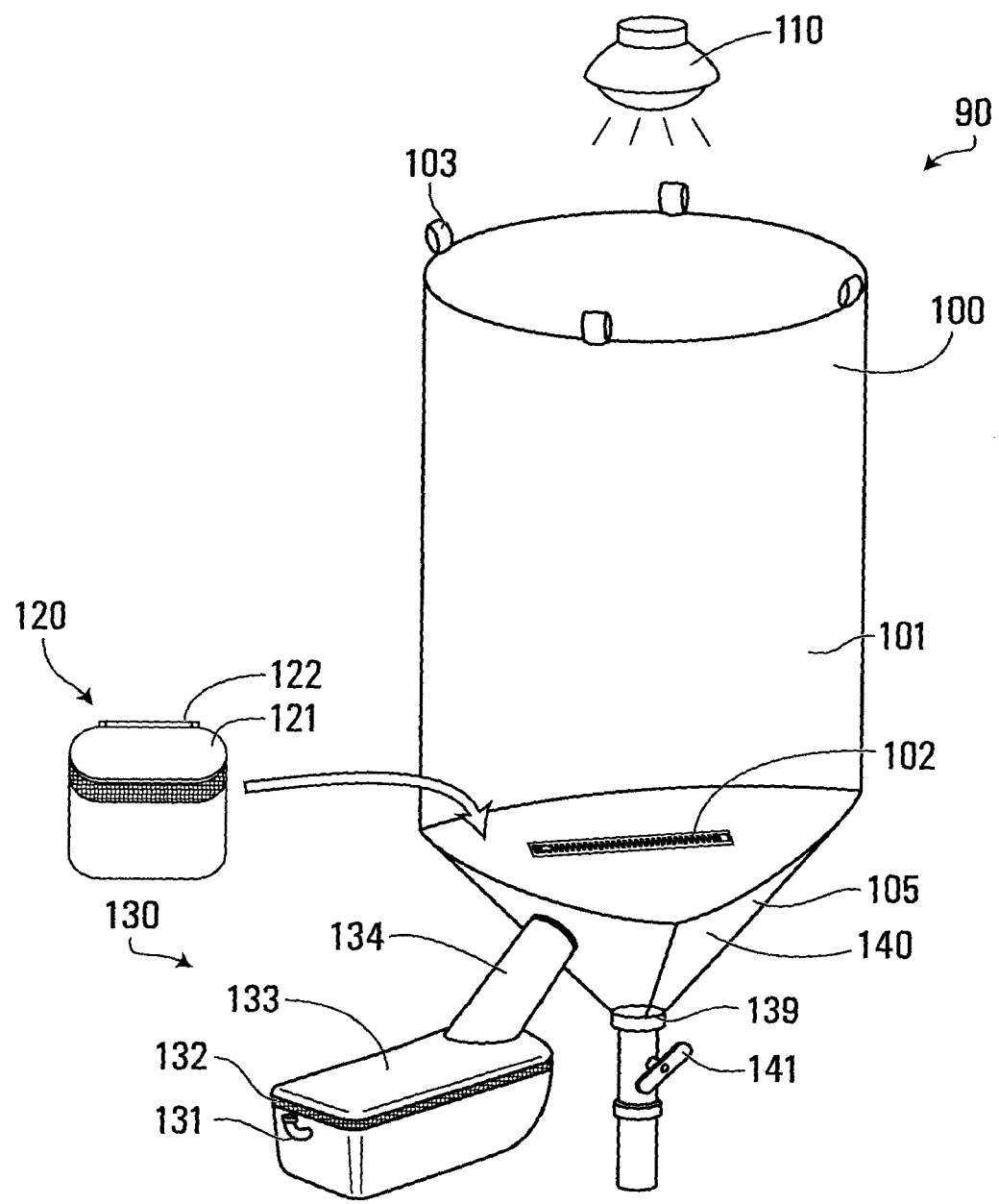
FIG. 1 is a perspective view of an apparatus for producing black soldier fly eggs according to a first embodiment of the invention.

Referring to FIG. 1, an apparatus for producing and isolating BSF eggs according to a first embodiment of the invention is shown generally at 90. The apparatus includes a mating chamber 100, an artificial light source 110, and an oviposition chamber 120 in communication with the mating chamber. Optional features include a pupation chamber 130 and a mort chamber 140, both of which can be placed in communication with mating chamber 100.

Mating Chamber.

Mating chamber 100 is defined by a plurality of walls, e.g. cylindrical upper wall 101 and lower conical wall 105. A person of ordinary skill in the art will understand, however, that mating chambers according to various embodiments of the invention may be defined by any number of walls, including a single wall. Walls 101 and 105 may be constructed from a plastic mesh material or other appropriate material. For example, walls 101 and 105 may be constructed of Lumite (Lumite Co., Baldwin, Ga.) because it is durable, heat- and UV-resistant. Further, light colored materials (e.g., white or yellow) may be used as they reflect fight and may also encourage BSF mating. The mating chamber 100 may be of any reasonable size and shape, for example a square or cylinder. Preferably, the bottom of the mating chamber is conical or v-shaped. For example, the mating chamber 100 may be generally cylindrical with a total volume of approximately 1.3 m$^3$. Further, and for example, the height of the mating chamber 100 will be limited (for example, to approximately 3 m or less) based on light diffusion from above. Alternatively, the generally cylindrical upper wall 101 (e.g., ~1.5 m in height, ~0.9 m in diameter) may be connected at the bottom to wall 105 which defines a funnel-shaped mort chamber 140.

Wall 101 includes a means of accessing the chamber 100 from the exterior, e.g. zipper 102 (e.g., ~90 cm long) located approximately 15 cm from the top of the mort chamber 140. However, a variety of sealable openings may be used. Additional access points may be provided as needed. For example, an approximate 0.15 m opening in wall 101 may provide an additional access for pupation chamber 130. The top of wall 101 may include a plurality of loops 103 for suspending the mating chamber 100 off the floor. Additional loops may be included on the inside of the mating chamber 100 from which plastic mesh or other suitable material may be suspended to increase the inner surface area for adult BSF to rest on (not shown in Figures).

The mating chamber 100 may be maintained at an air temperature of approximately 29° C. with a relative humidity of approximately 70%. Humidity may be maintained with, for example, a manual or automated humidifier; for example, a Sunbeam® humidifier may be employed. While adult BSF do not eat, they may be kept hydrated using a hydration system. Serving as an example, an Exo Terra® Monsoon RS4000 High Pressure Rain System may be installed and programmed to spray distilled water for approximately 12-16 seconds at 1 hour intervals.

Adult BSF may be added directly to the mating chamber 100 through an opening, e.g., through the zipper 102. Alternatively, adult BSF may be added indirectly to the mating chamber 100 by adding pupae or prepupae to pupation chamber 130 through the pupation chamber portal 131. Pupation chamber 130 may be in communication with mating chamber 130 by means of conduit 134. Accordingly, newly emergent adult BSF may migrate from the pupation chamber 130 to tubular conduit 134, and toward mating chamber 100.

Pupation Chamber.

The pupation chamber 130 may be constructed from any appropriate material, for example plastic or metal, according to any reasonable dimensions. For example, a plastic tote of approximate dimensions 2×1.5×1.5 feet may be used. The pupation chamber 130 may be kept at approximately 60-95% humidity, for example 80-90% humidity. The pupation chamber 130 may be kept at approximately and 25° C.-35° C., for example 28° C.-30° C. using a control system and probe (e.g., Zoo Med's Hydrotherm™). For example, humidity may be introduced with a fogging system (serving as an e.g., Zoo Med's Repti Fogger™ Terrarium Humidifier) and heat may be applied with a standard electric heating cable or ceramic heater or any other suitable heater. Dehumidification may be applied with a blower system.

BSF pupae or prepupae may be introduced to the pupation chamber 130 through a pupation chamber portal 131, which for example may be a PVC tubular conduit with cap located on the upper side of the pupation chamber 130. The top of the pupation chamber 130 may be covered with a mesh screen 132 that tapers to a tubular conduit 134 connecting the pupation chamber 130 with the mating chamber 100 or mort chamber 140. In the illustrated embodiment, conduit 134 connects the pupation chamber 130 with the mort chamber 140, which in turn is in communication with the mating chamber 100. The conduit 134 may be made of mesh or any other suitable material. A cover 133 may be placed over the mesh screen 132 to keep humidity inside and light out. The cover 133 may be made of plastic or any other suitable material. The opening to the conduit 134 is not blocked by the cover 133 so that when adult BSF emerge from pupation they are attracted to light shining from above through a sidewall of the tubular conduit 134, or light shining through tubular conduit 134 from mating chamber 100. Adult BSF may fly or walk through tubular conduit 134. The tubular conduit 134 may be angled at approximately 0 to 45 degrees relative to the base of the pupation chamber 130 to allow for light to enter, while maintaining an angle that matches the typical flight angle of BSF adults.

Referring to FIG. 3A, a pupation chamber according to various embodiments of the invention is shown generally at 330. Pupation chamber 330 includes a system of drawers 354 supported by a hollow frame 351. The system of drawers 354 allows for temporal (age) organization of the prepupae which enter chamber 330. The system further allows for easy removal of empty pupation exuviae after emergence has completed, and restocking of new prepupae. The system can provide drawer-specific control of environmental conditions (e.g., temperature and humidity). A yet further advantage of the drawer system is that it allows for expansion through the addition of additional drawer units into the system. Pupation chamber 330, for example, may be provided with eight (8) drawers, however a person skilled in the art will understand that only a subset of the total drawers may be used at any time.

Figure 3B:
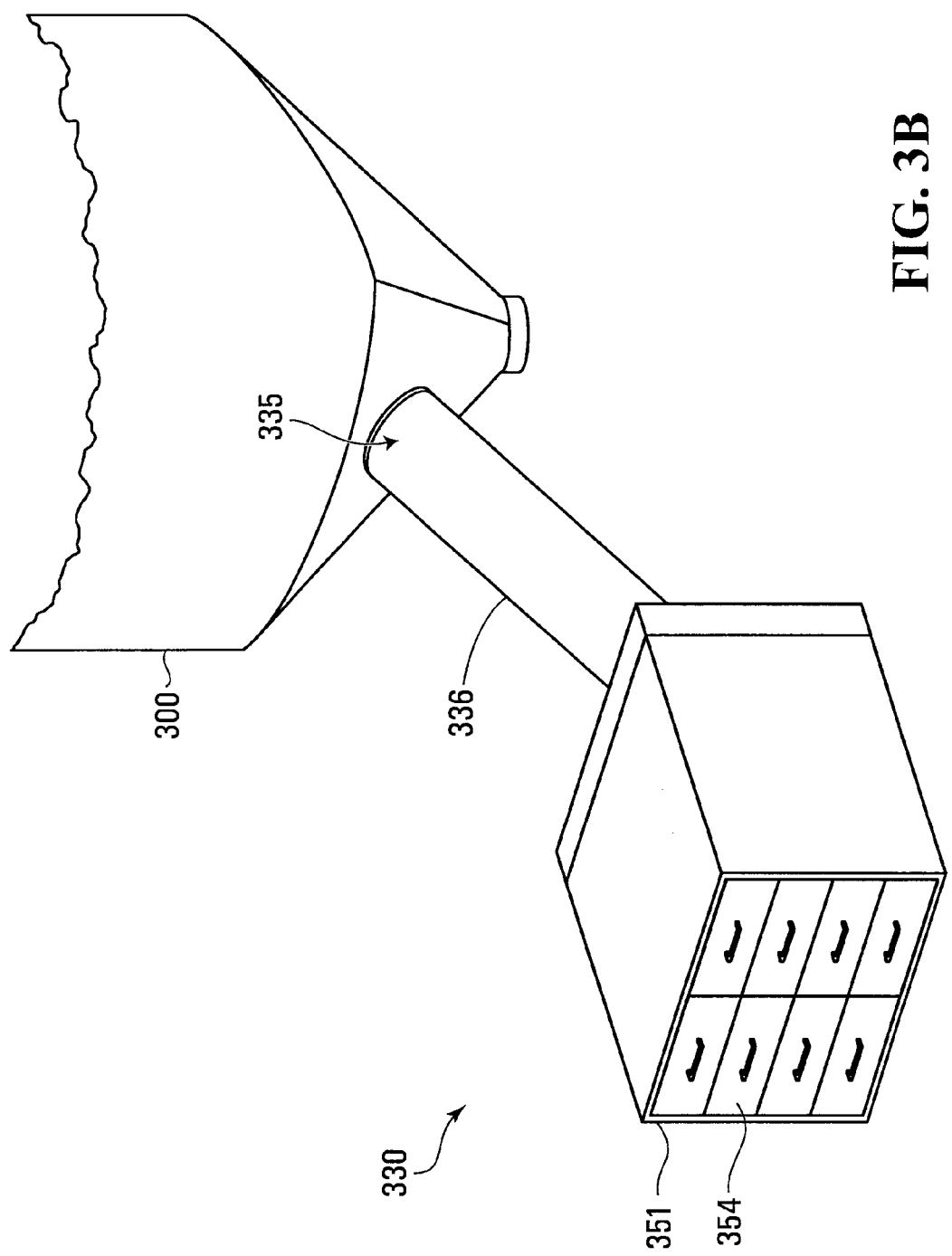
FIG. 3B is a perspective view of a pupation chamber utilizing a drawer system for use with various embodiments of the invention.

Referring still to FIG. 3A, pupation chamber 330 is connected from behind to the mating chamber 300 by tubular conduit 334. Tubular conduit 334 is made of a mesh material, however, a person skilled in the art will understand that it could be made of other materials, such as a non-mesh tube illustrated in FIG. 3B. Prepupae are loaded into each drawer 354 from the front end of the pupation chamber 330. A set of emergence holes (not shown) are positioned at the back of each drawer to provide an exit for the newly emerged adult BSF into conduit 334.

Adult BSFs are drawn to the exit holes at the back of the drawer due to illumination of conduit 334 by ambient light shining through the mesh, or the artificial light source of the mating chamber 300. Alternatively, an artificial lighting system external to mating chamber 300 can be employed to attract emerging adult BSFs from pupation chamber 330 into conduit 334. For example, LED lights can be provided on the interior of the conduit 334 to attract emerging adult BSFs. To assist in directing the movement of newly emerged adult BSFs, the pupation chamber 330 is enclosed within a dark fabric which only allows light to penetrate through exit holes at the back from conduit 334. Once in conduit 334, BSFs migrate through the conduit and into mating chamber 300 through opening 335 defined by a wall of the mating chamber.

Figure 4A:
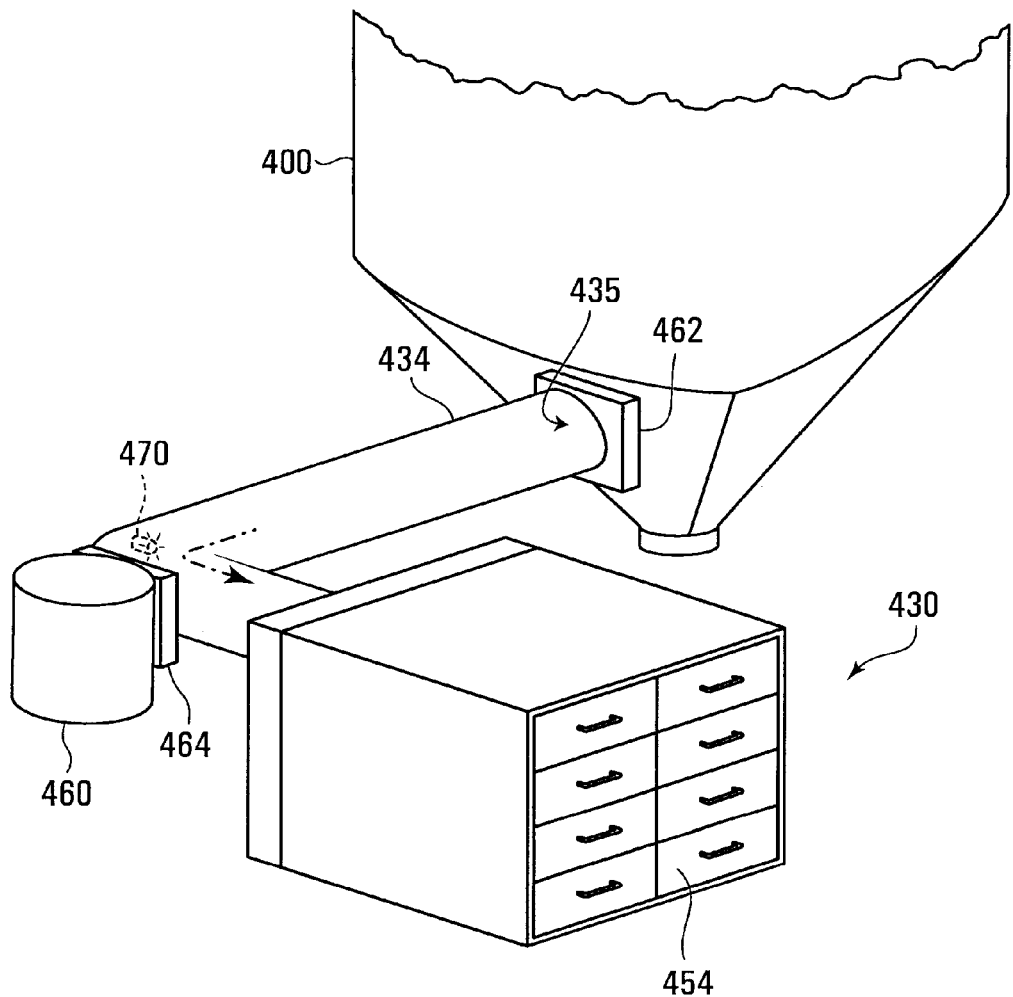
FIG. 4A is a perspective view of a pupation chamber utilizing a blower to blow emergent black soldier flies toward the mating chamber.
Figure 4B:
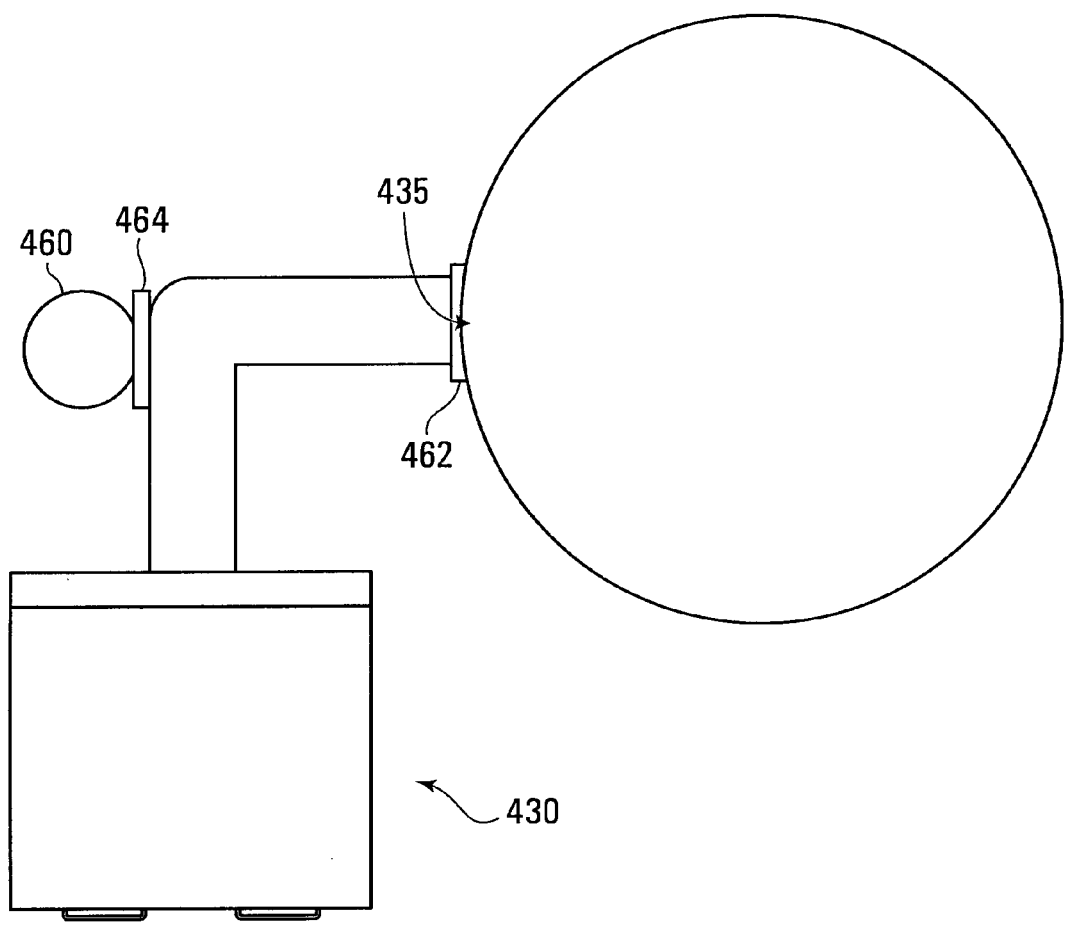
FIG. 4B is a top view of the pupation chamber illustrated in FIG. 4A.

Migration of newly emerged BSFs to the mating chamber does not have to be an entirely passive process as described above. FIG. 4 illustrates an embodiment of the invention in which a blower is used to blow BSFs in the conduit toward the mating chamber. In the illustrated embodiment, pupation chamber 430 is connected to mating chamber 400 by T-conduit 434. In the illustrated embodiment, T-conduit 434 is horizontal such that the entrance to the conduit from the emergence openings(s) of pupation chamber 430 is at the same height as mating chamber opening 435. However, a person skilled in the art will understand that conduit 434 need not be oriented horizontally, and that the entrance to the conduit and the maturation chamber opening 435 could be vertically offset from each other. Blower 460 is in communication with conduit 434, and configured to blow BSFs toward opening 435, and thus mating chamber 400. Attracted by light coming from conduit 434, newly emerged BSFs exit pupation chamber 430 into the conduit and are blown toward, and perhaps into, mating chamber 400. Blower 460 may be set on a timer to periodically blow, so as to allow for a plurality of BSFs to accumulate in the conduit 434 before they are blown toward the mating chamber 400. A check valve may used anywhere along the path between the blower 460 and the mating chamber 400 to prevent BSFs from retreating from the mating chamber to the conduit 434 or pupation chamber 430. In the illustrated embodiment, check valve 462 is positioned at opening 435. Check valve 464 opens due to pressure generated when blower 460 is in operation. Check valve 462 closes due to the decrease in pressure when blower 460 is off, which ensures that gravid female BSFs cannot retreat from the mating chamber 400 to oviposit eggs in the connector 434 or pupation chamber 430. Another check valve 464 may be positioned to seal blower 460 from conduit 434 to prevent flies from settling around or getting stuck in the blower. The conduit 434 may be shaped such that a venturi effect creates suction to aid the movement of flies from the pupation chamber 430 to the mating chamber 400. Blower 460 may also help ventilate the pupation chamber 430 and keep prepupae at the desired humidity and temperature. Alternatively, or in combination with blower 460, an artificial lighting system external to mating chamber 400 can be employed to attract emerging adult BSFs from pupation chamber 430 into conduit 434. For example, LED light 470 can be provided on the interior of the conduit 434 to attract emerging adult BSFs.

Figure 5:
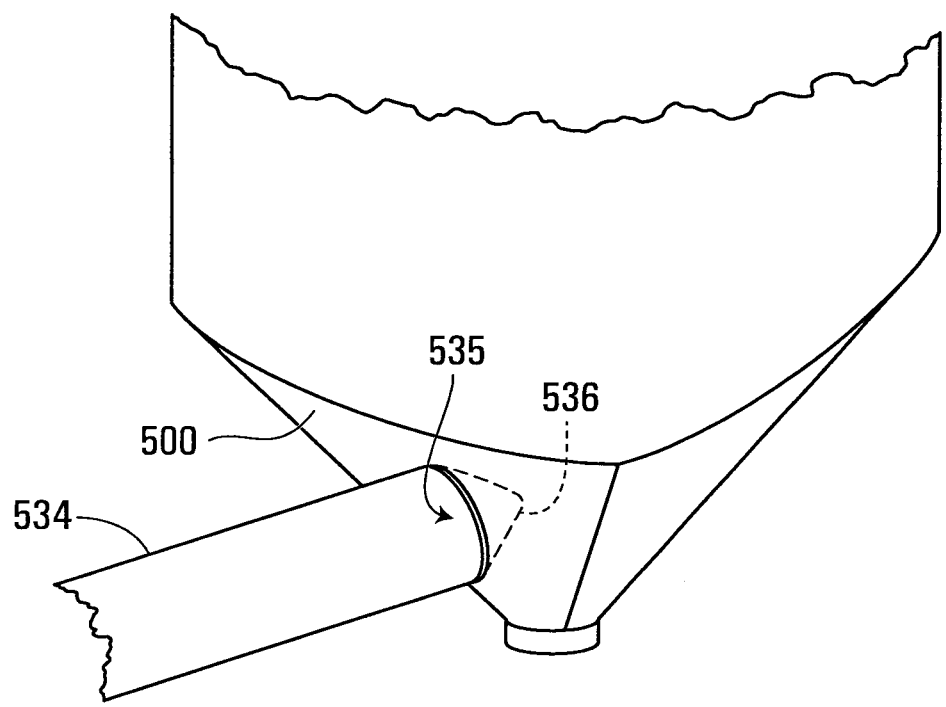
FIG. 5 is a perspective view of a connection between a pupation chamber and a mating chamber including a funnel trap for preventing retreat of black soldier flies from the mating chamber.
Figure 6:
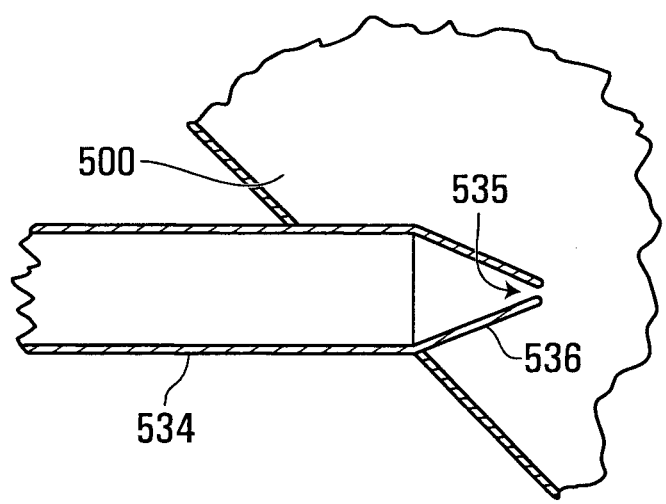
FIG. 6 a cross-sectional view of the connection illustrated in FIG. 5.

A person skilled in the art will further understand that alternative structures can be used, both with passive systems or systems employing blowers, to prevent retreat of BSFs from the mating chamber. FIGS. 5 to 8 illustrate the use of a one-way passage or duct to inhibit or prevent retreat of BSFs from the mating chamber 100. One-way passages will generally have a wide entrance and taper towards a exit of sufficient size and shape to permit passage of a BSF through, but sufficiently narrow and acute as to inhibit subsequent re-entry of the BSF into the one-way conduit. In one alternative, the one-way conduit includes a funnel, which may be generally frustoconical in shape (although other shapes may be contemplated). Referring to FIGS. 5 and 6, opening 535 to the mating chamber 500 is defined by funnel 536 which tapers toward the mating chamber 500. Accordingly, BSFs are funneled into chamber 500, and cannot retreat into conduit 534.

Figure 7:
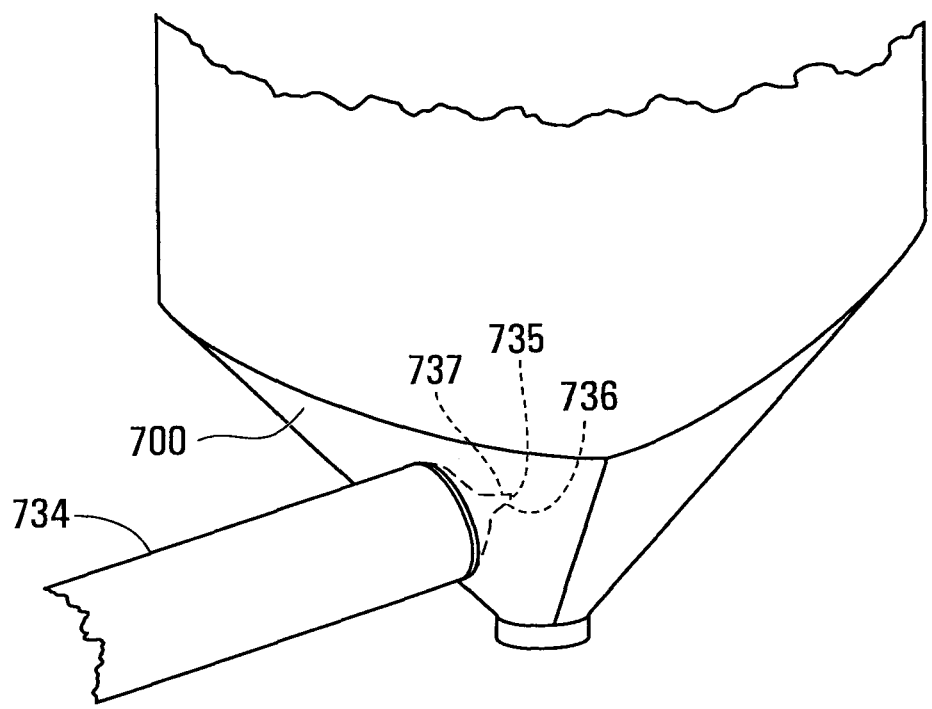
FIG. 7 is a perspective view of a connection between a pupation chamber and a mating chamber including a tapered slot with offset end edges for preventing retreat of black soldier flies from the mating chamber.
Figure 8:
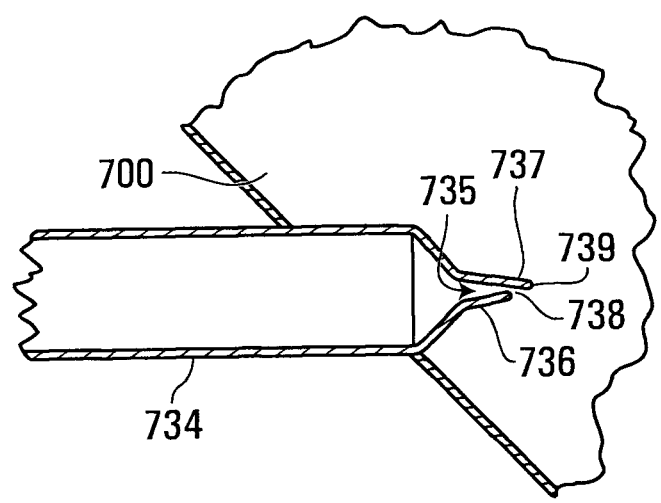
FIG. 8 a cross-sectional view of the connection illustrated in FIG. 7.

In another alternative illustrated in FIGS. 7 and 8, the one-way passage may be include a tapered slot comprising opposing walls 736 and 737 which taper toward each other from the entrance to the exit, i.e. slit 735. As seen in FIG. 8, edge portions 738 and 739 of walls 736 and 737, which define slit 735, are offset and extend with mating chamber 700.

The illustrated one-way conduits may serve to prevent BSFs from retreating into the conduit for several reasons. A BSF may be unable to articulate its abdomen and thorax to an angle less than that required to make it through the hole 535 in FIG. 6 or slit 735 in FIG. 8. BSFs may be unable to fly directly into the hole 535 or slit 735 where the width of the wingspan approaches or is greater than the width of the hole or slit. Where the overlapping edge portion of slit 735 extends beyond the underlapping edge portion 738 by less than the length of a BSF, a BSF may be unable to easily land on the underside of the overlapping edge 739, and thus be discouraged from landing parallel to the slit 735.

While one-way conduits have been illustrated in association with the mating chamber opening, it will be appreciated that the one-way conduits could be positioned anywhere in the conduit between the pupation chamber and the mating chamber opening and still achieve a desired effect of preventing retreat of BSFs, especially gravid BSFs, toward the pupation chamber.

Furthermore, while the illustrated embodiments show the use of conduits to connect mating chambers with external pupation chambers, a person skilled in the art will understand that it is sufficient that the pupation chamber and the mating chamber are in communication with each other. Accordingly, in a simplified embodiment of the invention, the pupation chamber may be positioned directly within the mating chamber. BSF pupae or prepupae may be introduced to the pupation chamber outside the mating chamber. Once the BSF pupae or prepupae are introduced into the pupation chamber, the pupation chamber can be placed within the mating chamber. Provided that the pupation chamber remains in communication with the mating chamber, e.g. by way of an emergence hole(s) in the walls or ceiling that define the pupation chamber, and that light from the mating chamber can penetrate into the pupation chamber to attract newly emerged BSFs adult from the pupation chamber to the mating chamber, a further conduit to connect the pupation chamber and mating chamber is not necessary. Nevertheless, one way passages or ducts may be used in combination with emergence holes to prevent BSF adults from re-entering the pupation chamber from the mating chamber.

Figure 2:
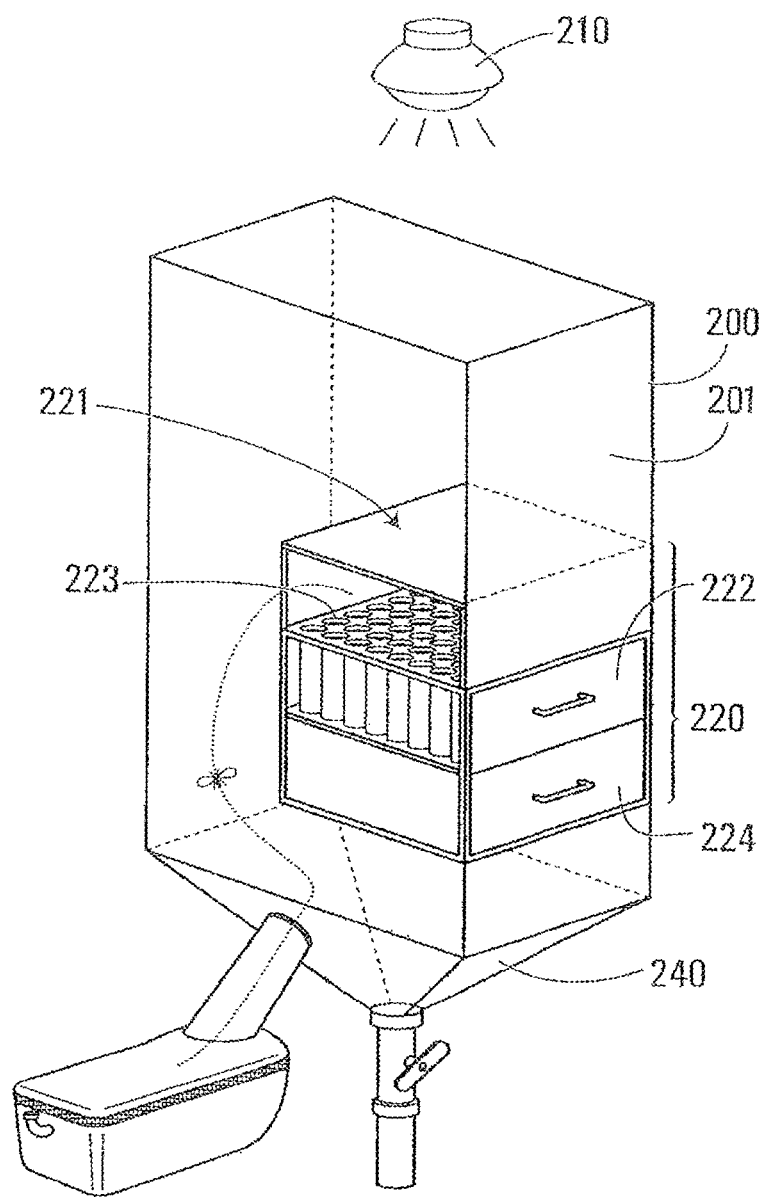
FIG. 2 is a perspective view of an apparatus for producing black soldier fly eggs according to a second embodiment of the invention in which the oviposition chamber is accessible from outside the apparatus using a drawer system.
Figure 9:
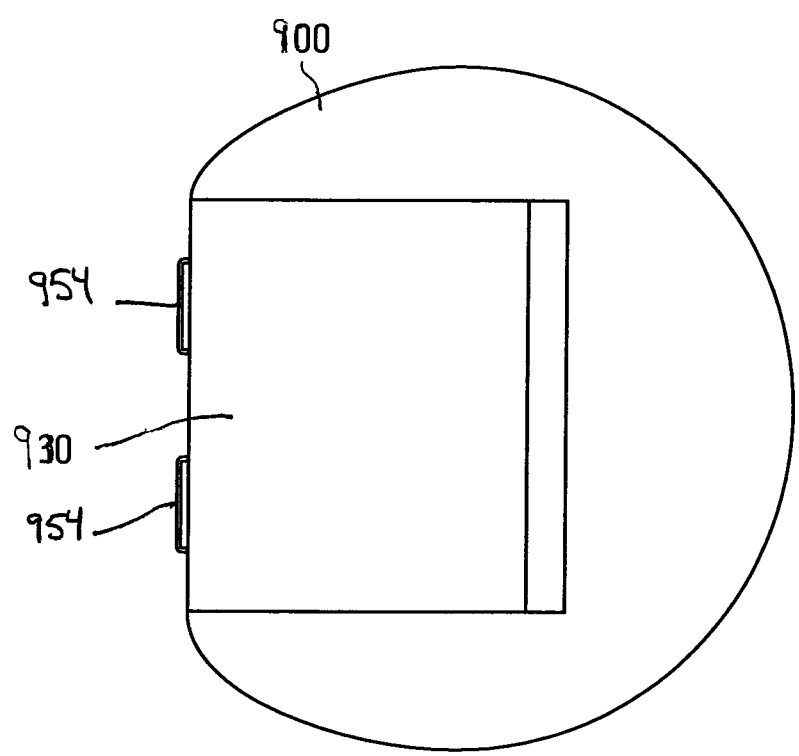
FIG. 9 is a cross-sectional top view of an embodiment of the invention in which the pupation chamber is positioned within the mating chamber and comprises a drawer system by which pupae and prepupae may be intoducted to the pupation chamber from the exterior of the mating chamber.

As a further alternative design for a pupation chamber, and referring to FIG. 9, mating chamber opening of mating chamber 900 may be designed to accommodate drawers 954 of pupation chamber 930, such that the pupation chamber may be positioned within the mating chamber yet the contents of the drawers may be accessed from the exterior of the mating chamber. Such design, which may be similar to that discussed below for the oviposition chamber as illustrated in FIG. 2, facilitates the introduction of the pupae and prepupae to the system without entering the mating chamber 900 or allowing adult BSF to escape. The pupation chamber 930 may be sewn into the mating chamber and supported from the mating chamber frame structure or supported from above by rope, chain or rods, or other suitable means.

Referring again to FIG. 3, the capacity of prepupae for each drawer 354 of the drawer system is dependent on the desired population size for the mating chamber 300. A rotating pupae input system (based on the development time required for prepupae to mature into adults) can be utilized to sequence the availability of empty drawers as desired. Further, individual environmental temperature control devices may be installed into each drawer 354 for controlling environmental conditions therein.

Mort Chamber.

Referring again to FIG. 1, once in the mating chamber 100, adult BSF live approximately 7 to 10 days. On about day 2-4, females mate with males. On about days 3-5 they lay eggs. Around day 7 to 10, BSF die and collect in the funnel-shaped mort chamber 140 at the bottom of the mating chamber 100. At the bottom of the mort chamber 140 is an opening 139 (for e.g., 0.15 m in diameter) fitted with a manual or automated valve 141, which facilitates the daily or periodic collection of mortalities. Alternatively, if the mort chamber is v-shaped such that the mortality chamber is a long trough, a trough cleaning mechanism may be used to sweep mortalities to one end of the trough for collection through a gate or valve.

Artificial Light Source.

Referring still to FIG. 1, an artificial light source 110 is shown suspended above the mating chamber 100. There may be more than one artificial light source. For example, the light source 110 may be placed approximately 0.15 m above the top of the mating chamber 100. For example, a 500 W quartz-iodine light source (Model QVF135, Philips Lighting Ltd.) is reported to provide a spectrum between 350-2500 nm at 135 µmol·m$^{-2}$·s$^{-1}$ light intensity. This light reportedly achieved 61.9% BSF mating success relative to natural sunlight under conditions of 28-30° C., 60-90% humidity, and access to drinking water via a spray every 2-3 hours (Zhang et al., 2010). Reproducing these same conditions in-house achieved 51% mating success (see Example 1, Table 2 herein). As described below, it was discovered that the addition of a halogen light source (e.g., a 50 W Exo Terra® Sunglo Halogen bulb or 50 W Halogen Neodymium Daylight bulb), which produces low intensity UBA and UVB, visible, and infrared wavelengths to the quartz-iodine light source improved mating success. The highest degree of mating success was observed when a 300 W quartz-iodine light was used in combination with a 50 W halogen light (see: Example 1, Table 2 herein). Light fixtures were placed approximately 30 cm from their center points and angled toward each other at an angle of 15 degrees such that the wavelengths from the emitted light sources overlap. In another embodiment, natural sunlight may be used as a supplemental light source and/or a single light source may be used that emits a broader range of wavelengths than the combination described above, but is modified with filters to provide substantially the same intensities and wavelengths as the combination of the quartz-iodine and halogen light sources. A light and darkness cycle may be used to emulate day and night. Serving as a non-limiting example, the total light source (both bulbs) may be turned on for a light period of 9 hours from 0800 h to 1700 h, and turned off for a darkness period of 15 hours from 1701 h-0759 h.

Oviposition Chamber.

Referring still to FIG. 1, the oviposition chamber 120 may be placed inside the mating chamber 100; for example, the oviposition chamber 120 may be supported by a rack (not shown in FIG. 1) affixed to the walls of the mating chamber 100 or it may be supported from the bottom or top of the mating chamber 100. Alternatively, the oviposition chamber 120 may be separate but connected to the mating chamber 100, so long as the mating chamber and oviposition chamber are in communication. FIG. 1 shows an example of an oviposition chamber 120 constructed of a plastic bucket, with a lid 121. Serving as a non-limiting example, the oviposition chamber lid 121 is propped open from the lid hinge 122 with a wire stopper. This creates an entrance and exit to the oviposition chamber 120, and also creates a dark environment which promotes ovipositing by the female BSF. Egg laying materials are placed on the inner walls of the bucket. For example, the egg laying materials may be blocks of corrugated cardboard; female BSF will oviposit eggs into the openings of individual "flutes" in the cardboard. Serving as a non-limiting example, the dimensions of flute openings may be approximately 3 mm×3 mm. Further, and for example, cardboard blocks may be constructed from stacks of three strips of approximately 3×10 cm cardboard held together with tape, but leaving the flute openings uncovered. Further, egg laying material may be plastic or metal with equivalent sized holes ranging in size from 2-4 mm in diameter. The shape of the hole openings may be circular, elliptical, half circles, square or variations thereof. An attractant is placed in the bottom of the bucket to draw gravid (i.e., pregnant) female BSF to the oviposition chamber 120. An example of an attractant is a saturated 1:1 mixture of Gainesville diet (Hogsette, 1985) mixed with BSF larvae leachate and BSF castings. Other attractants can include fermenting grain, such as corn brewery grain, manure, decomposing food waste, BSF larvae and/or eggs. Any or all of these in various combinations will attract gravid female BSFs.

Referring to FIG. 2 now, an alternative design for an oviposition chamber is shown generally at 220. As alluded to above, wall 201 of mating chamber 200 defines an additional opening for accommodating drawers 222 and 224 of oviposition chamber 220, such that the oviposition chamber may be positioned within the mating chamber yet the contents of the drawers may be accessed from the exterior of the mating chamber. This design facilitates the collection of BSF eggs without entering the mating chamber 200 or allowing adult BSF to escape. The oviposition chamber 220 may be sewn into the mating chamber 200 and supported by a cross piece (not shown in FIG. 2) from the mating chamber 200 frame structure or supported from above by rope, chain or rods, or other suitable means. Serving as a non-limiting example, the oviposition chamber 220 may be sewn into the mating chamber 200 at a height of approximately ⅓ of the total mating chamber 200 height from the mort chamber 240. Gravid female BSFs prefer to oviposit out of direct light; accordingly, a floating roof 221 may be used to provide shade from the artificial light source 210 and keep egg laying material dry and away from the mist. The top drawer 222 may contain egg-laying materials 223 consisting of, for example, vertically-oriented plastic or cardboard flutes or tubes that are open at both ends (as detailed herein). The bottom section of the top drawer may be perforated to allow for the scent of attractant to diffuse from the bottom drawer into the top drawer 224. A sweeper (not shown in FIG. 2) may be fixed to the frame of the oviposition chamber 220 to gently remove any adults that may be laying eggs or resting on the egg laying material as the drawer is opened. The bottom drawer may contain a saturated 1:1 mixture of Gainesville diet mixed with BSF larvae leachate and BSF castings, or other suitable attractants (as detailed herein), to draw gravid female BSFs to the egg laying materials 223 above it. A metal sheet (not shown in FIG. 2) may be used to slide between the top and bottom drawers (222 and 224, respectively) to cover the bottom drawer 224, when the top drawer 222 is removed for egg collection or when the attractant is being replaced to prevent undesired adults accessing and/or landing in the attractant. Alternatively, a single drawer may be used whereby the vertically oriented tubes are held above the attractant with tabs, such that the top of the tubes are flush, i.e. lay in substantially a common plane, with the top of the drawer. Drawers 222 and 224 are located tight to the frame to discourage females from laying eggs in crevices and the frame is enclosed on the sides and bottom to prevent adults escaping when drawers are opened.

The egg laying materials 223 containing eggs may be collected within approximately 0-24 hours after the eggs have been laid.

Example 1

Induction of BSF Mating Using Visible and UV Light

Methodology for Light Intensity Measurements.

Light intensities of visible light, UVA+B, and UVB where measured with an Apogee Instruments Inc., Quantum meter, Model MQ-100, a Solartech, Inc. Solarmeter Model 6.7, Total UV (A+B), and a Solartech, Inc. Solarmeter Model 6.2, UVB, respectively. The Quartz-iodine bulb and Halogen Neodymium Daylight bulb were approximately 30 cm apart from their center and tilted on an approximate 15 degree angle such that their respective light beams overlapped, with light readings made at approximately 50 cm below the middle distance between the two bulbs. For individual bulbs, the reading was made approximately 50 cm directly below the bulb as described by Zhang et al. (2010). For light measurements, lights were suspended above the floor by approximately 60 cm; the light meter was secured to a holder such that the sensor of the meter was approximately 50 cm from the bulb. The holder was moved along the floor until the peak intensity was measured.

Methodology for Statistical Analyses.

The mating success per treatment was calculated by dividing the total number of egg clutches laid by half the total number of flies that entered into the experimental cage on days 0 to 8 (the last two days of flies added to the cage were not taken into account). This calculation is based on reports that (i) *H. illucens* females generally do not oviposit unless they have mated and been fertilized (Tomberlin and Sheppard, 2002; Tomberlin et al., 2002); (ii) the percentage of females found in laboratory BSF colonies is around 55.2% (Tomberlin et al. 2002), and (iii) flies added during the last two days of the experiment would have laid eggs two days later (i.e., after the treatment was finished (Tomberlin and Sheppard, 2002; and Tomberlin et al., 2002). Moreover, Pearson's correlation coefficient between mating success and mean egg clutches laid per treatment was 0.9510, which indicates a strong relationship between both variables.

Results.

Attempts using other type of lights for stimulating mating in the BSF such as using a 40-Watt Sylvania Gro Lux® (Tomberlin and Sheppard, 2002), a 430-watt Pro Ultralight Light System (Tomberlin and Sheppard, 2002) or a 450-watt rare earth light (Engineering University Infrared Technology Research institute, Harbin, Heilung-kiang, China; Zhang et al., 2010) resulted in no matings. The only other artificial light source published to successfully stimulate mating so far is the 500-watt quartz-iodine lamp (Zhang et al., 2010), but the highest mating success achieved was 61.9% of that observed in the sunlight treatment. The results of the experiment reported here do not have a sunlight control, but the same 500-watt quartz-iodine lamp used by Zhang et al. (2010) resulted in 50.76% mating success, whereas 69.53% of the females released in replicate one and 88.16% of the females in replicate two of treatment Light 1 mated, and 95.91% of those released in treatment Light 4 mated (see Table 2 herein). Thus, these results suggest that the addition of a 50 W Halogen Neodymium Daylight lamp to a 300 or 500 quartz-iodine lamp when maintaining a colony of *H. illucens* does significantly increase matings. However, the addition of a 100 W Halogen Neodumium Daylight lamp was found to inhibit mating relative to the 500 W Quartz Iodine by itself. This suggests that the full range of wavelengths (350-700 nm) is required for optimal mating and there exists an optimal balance between the intensity of infrared (700 nm+), visible light (450-700 nm) and ultraviolet light (UVA—315-400 nm, UVB—280-315 nm). For example, a ratio of between 3.5:1 and 4:1, Visible ($\mu mol \cdot m^{-2} \cdot s^{-1}$):UVA+B ($\mu W \cdot cm^{-2} \cdot s^{-1}$) (see: Table 1). Although the 500-watt quartz-iodine lamp emits the full-spectrum of light, much of the UV light is filtered by tempered glass used in the flood light fixture. Thus, the addition of the 50 W Halogen Neodymium Daylight lamp may compensate for the UV filtering effect of the tempered glass. The 50 W Halogen Neodymium Daylight lamp also emits visible and infrared light which may be contributing to mating behaviour. It is possible that the 500-Watt Quartz Iodine provides optimal visible light, but is slightly deficient in UV light, whereas the rare earth lamp provides too high an intensity of UV light and lacks adequate visible light for optimal mating.

Optimal visible and UV light intensity for BSF adult mating is between 200 and 400 $\mu mol \cdot m^{-2} \cdot s^{-1}$ and 50 and 100 $\mu W \cdot cm^{-2} \cdot s^{-1}$ UVA+B (peak intensities, 50 cm below the bulb(s)) (see: Table 1 and Table 2).

TABLE 1

Maximum light intensities of visible, UVA + B, UVB for various light combinations.

|  | Visible (450-700 nm) Intensity $\mu mol m^{-2} s^{-1}$ | UVA + B (315-400 nm) Intensity $\mu W\, cm^{-2} s^{-1}$ | UVB (280-315 nm) Intensity $\mu W\, cm^{-2} s^{-1}$ | Ratio (Visible - $\mu mol m^{-2} s^{-1}$:UVA + B- $\mu W\, cm^{-2} s^{-1}$) |
|---|---|---|---|---|
| 500 W Quartz Iodine | 238 | 58 | 0 | 4.1:1 |
| 500 W Quartz Iodine + 50 W Sunglow Halogen | 370 | 100 | 1 | 3.7:1 |
| 300 W Quartz Iodine + 50 W Sunglow Halogen | 310 | 80 | 1 | 3.8:1 |
| 50 W Sunglow Halogen | 215 | 63 | 1 | 3.4:1 |
| 100 W Sunglow Halogen | 600 | 240 | 7 | 2.5:1 |

There was a significant difference in the mean number of matings and egg clutches laid per day among treatments (see Table 2). Treatment Light 1 (500 W-quartz+50 W-halogen) rendered the highest number of matings observed, while in treatment Light 4 (300 W-quartz+50 W-Halogen) females oviposited the most. Mating success was also the highest in Light 4, followed by Light 1. The average temperature did not differ among treatments (p=0.4095; see Table 3), but there were significant differences in humidity (p<0.001; see Table 4 for homogeneous groups). However, in this experiment there was no significant correlation between humidity and mating observations or egg clutches laid. There were significant differences in the mean number of matings per observation time across treatments. Most data were normal except the matings of Light 3 (300 W-quartz+100 W-halogen) and the female mortalities of Control (see Table 5 for Shapiro-Wilk's normality tests). In contrast, all matings per observation time behaved normally (except those of 9:00 a.m. in Light 1, see Table 3).

TABLE 2

Mean of each variable measured per treatment.

| TREATMENT | Mean number of matings* | Mean number of clutches* | Mating success (%) | Mean number of morts Males* | Mean number of morts Females* | 1 Mean temperature* (° C.) | 2 Mean humidity* (%) | Mean number of matings per observation time 8:00 | 9:00 | 10:00 | 11:00 | 12:00 | 13:00 |
|---|---|---|---|---|---|---|---|---|---|---|---|---|---|
| Control (500-quartz) | 3.3 ± 1.4 | 5.0 ± 3.8 | 50.76 | 6.0 ± 4.9 | 4.8 ± 2.7 | 26.90 ± 0.99 | 32.7 ± 4.8 | 0.6 | 0.4 | 0.7 | 0.4 | 0.5 | 0.7 |
| Light 1 Replicate 1 (500-quartz + 50 Halogen) | 6.9 ± 5.6 | 8.1 ± 5.6 | 69.53 | 9.0 ± 5.3 | 8.2 ± 3.8 | 27.45 ± 1.34 | 31.7 ± 1.0 | 0.8 | 1.3 | 1.8 | 1.6 | 0.8 | 0.6 |
| Light 1 Replicate 2. (500-quartz + 50 Halogen) | 6.1 ± 3.0 | 7.3 ± 6.3 | 88.16 | 2.0 ± 1.3 | 1.8 ± 2.2 | 27.37 ± 1.59 | 44.4 ± 4.6 | 0.2 | 0.6 | 1.4 | 1.3 | 1.1 | 1.5 |
| Light 2 (500-quartz + 100 Halogen) | 2.6 ± 2.2 | 1.7 ± 1.6 | 14.29 | 8.8 ± 5.3 | 8.0 ± 3.0 | 27.57 ± 0.75 | 34.1 ± 3.6 | 0.1 | 0.4 | 0.3 | 1.0 | 0.5 | 0.3 |
| Light 3 (300-quartz + 100 Halogen) | 5.7 ± 3.0 | 6.2 ± 3.7 | 57.94 | 7.1 ± 4.5 | 6.3 ± 3.4 | 27.08 ± 0.57 | 36.9 ± 3.2 | 0.3 | 1.0 | 1.0 | 1.2 | 1.0 | 1.2 |
| Light 4 (300-quartz + 50 Halogen) | 4.7 ± 2.1 | 8.2 ± 5.0 | 95.91 | 3.3 ± 2.0 | 4.6 ± 1.8 | 26.72 ± 1.66 | 43.7 ± 4.8 | 0.1 | 0.9 | 0.8 | 1.3 | 0.8 | 0.8 |

*Standard deviation of these variables is reported after the ± symbol.

The apparatus(es) and methods detailed herein can be used in a more expansive "lifecycle" of the BSF. For example, BSF eggs generated using the apparatus(es) and methods detailed herein can be introduced to a digester that contains organic waste materials (for example, fruits, vegetables and fish offal). The BSF life cycle can proceed with the BSF larvae converting organic waste which is present in the digester. The life cycle can further proceed with BSF larvae becoming prepupae. Prepupae or larvae can be processed for further purposes (for e.g., livestock (aquatic or terrestrial), pet feed, or even foodstuffs for human consumption). Further, prepupae can be introduced into a self-contained hatchery apparatus (as described herein) for generating BSF eggs. Accordingly, it will be appreciated that a digester which supports organic waste materials can be used in association with the apparatus(es) and methods detailed herein.

REFERENCES

1. Bradley, S. W. and Sheppard, D. C. 1984. House Fly Oviposition Inhibition by Larvae of *Hermetia illucens*, the Black Soldier Fly. *Journal of Chemical Ecology*, 19, 853.
2. Erickson, M. C., M. Islam, C. Sheppard, J. Liao, and M. P. Doyle. 2004. Reduction of *Eschericia coli* 0157:H7 and *Salmonella enterica* serovar Enteritidis in chicken manure by larvae of the black soldier fly. J. Food Protection. 67: 685-690.
3. Furman, D. P., R. D. Young, and E. P. Catts. 1959. *Hermetia illucens* (Linnaeus) as a factor in the natural control of *Musca domestica Linnaeus*. J. Econ. Entomol. 52: 917-921.
4. Hogsette, J. A. 1985. New diets for production of house flies and stable flies (Diptera: Muscidae) in the laboratory. J. Econ. Entomol. 85: 2291-2294.
5. Liu, Q., Tomerblin, J. K., Brady, J. A., Sanford, M. R., and Yu, Z. 2008. Black Soldier Fly (Diptera: Stratiomyidae) Larvae Reduce *Escherichia coli* in Dairy Manure. *Environ. Entomol.* 37(6): 1525-1530.
6. Sheppard, D. C J. K.; J. K. Tomberlin, J. A. Joyce, B. C. Kiser & S. M. Sumner. 2002. Rearing Methods for the Black Soldier Fly (Diptera: Stratiomyidae). *J. Med. Entomol.* 39(4): 695-698.
7. Tomberlin, J. K., Alder, P. H., and Myers H. M. 2009. Development of the Black Soldier Fly (Diptera: Stratiomyidae) in Relation to Temperature. *Environ. Entomol.* 38: 930-934.
8. Tomberlin, J. K. & D. C. Sheppard. 2002. Factors Influencing Mating and Oviposition of Black Soldier Flies (Diptera: Stratiomyidae) in a Colony. *J. Entomol. Sci.* 37(4): 345-352.
9. Tomberlin, J. K., D. C. Sheppard & J. A. Joyce. 2002. Selected Life-History Traits of Black Soldier Flies (Diptera: Stratiomyidae) Reared on Three Artificial Diets. *Ann. Entomol. Soc. Am.* 95(3): 379-386
10. Zhang, et al. 2010. An artificial light source influences mating and oviposition of black soldier flies, *Hermetia illucens*. J. Insect Sci. 10:1-7.

We claim:

1. A method of inducing black soldier flies (BSFs) to mate, comprising:
   providing at least one male BSF and at least one female BSF to a mating chamber;
   illuminating the mating chamber with artificial light comprising at least one wavelength in a visible spectrum and at least one wavelength in an ultraviolet spectrum to induce the at least one male BSF and the at least one female BSF to mate, wherein the artificial light is provided by an artificial light source comprising a 300 to 500 W quartz-iodine lamp for generating the at least one wavelength in the visible spectrum and a 50 W halogen lamp for producing the at least one wavelength in the ultraviolet spectrum.

2. The method of claim 1, wherein:
   the artificial light comprises visible light having a visible light intensity that is less than 400 $\mu mol \cdot m^{-2} \cdot s^{-1}$ and ultraviolet light having an ultraviolet light intensity that is less than 100 $\mu W \cdot cm^{-2} \cdot s^{-1}$.

3. The method of claim 1, further comprising providing a pupation chamber in communication with the mating chamber.

4. The method of claim 3, further comprising a pupation chamber shade for shading pupae from the at least one artificial light source.

5. The method of claim 3, wherein communication between the pupation chamber and the mating chamber is provided by a conduit connecting the pupation chamber to the mating chamber via a mating chamber opening.

6. The method of claim 5, further comprising providing a blower in communication with the conduit for blowing BSFs in the conduit toward the mating chamber.

7. The method of claim 6, wherein the conduit further comprises a check valve through which the BSFs must pass in order to access the mating chamber, wherein the check valve opens in response to a force generated by the blower.

8. The method of claim 7, further comprising a conduit light source configured to illuminate a portion of the conduit to attract migration of the BSFs from the pupation chamber to the conduit.

9. The method of claim 5, wherein the conduit includes a one-way passage through which BSFs must pass in order to access the mating chamber.

10. The method of claim 9, wherein the one-way passage includes a funnel trap through which black soldier flies must pass in order to access the mating chamber, wherein the funnel trap tapers toward the mating chamber.

11. The method of claim 1, further comprising means for removing dead BSFs from the mating chamber.

12. The method of claim 11, wherein the means for removing dead BSFs from the mating chamber includes a sealable opening adjacent a bottom of the mating chamber.

13. The method of claim 12, wherein at least one wall defining the mating chamber tapers toward the sealable opening.

14. The method of claim 1, further comprising:
   attracting gravid BSFs to an oviposition chamber in communication with the mating chamber, wherein the oviposition chamber is configured to receive eggs from the gravid BSFs;
   shading the gravid BSFs in the oviposition chamber to induce the gravid BSFs to oviposit eggs; and
   collecting eggs oviposited by the gravid BSFs.

15. The method of claim 14, wherein the eggs oviposited by the gravid BSFs are collected in a collector comprising a plurality of substantially vertical flutes or tubes.

16. The method of claim 14, wherein the oviposition chamber further comprises an attractant for attracting the gravid BSFs.

17. The method of claim 16, wherein the oviposition chamber further comprises an upper drawer and a lower drawer, wherein each of the upper drawer and the lower drawer is configured to open to an exterior of the mating chamber, and wherein the eggs oviposited by the gravid BSFs are collected in a collector is situated on the upper drawer and the attractant is situated on the lower drawer.

* * * * *